United States Patent [19]

Rabin et al.

[11] Patent Number: 5,445,942
[45] Date of Patent: Aug. 29, 1995

[54] AMPLIFICATION ASSAY FOR HYDROLASE ENZYMES

[75] Inventors: Brian R. Rabin, Potters Bar; Stuart Harbron, Berkhamstead; Hendrikus J. Eggelte, Brunswick Square; Michael R. Hollaway, deceased, late of Brunswick Square; Ann Holloway, legal representative, Surrey, all of United Kingdom

[73] Assignee: London Biotechnology Limited, London, Great Britain

[21] Appl. No.: 15,287

[22] Filed: Jan. 13, 1993

Related U.S. Application Data

[63] Continuation of Ser. No. 646,711, filed as PCT/GB89/00877, July 31, 1989, abandoned.

[30] Foreign Application Priority Data

Aug. 2, 1988 [GB] United Kingdom ............... 8818336
Mar. 8, 1989 [GB] United Kingdom ............... 8905347

[51] Int. Cl.$^6$ .................. C12Q 1/34; C12Q 1/28; C07H 19/06
[52] U.S. Cl. ...................................... 435/18; 435/7.7; 435/28; 435/810; 435/975; 536/26.25
[58] Field of Search .................. 435/7.4, 7.7, 14, 18, 435/21, 25, 26, 28, 810, 975; 536/24, 26, 26.25

[56] References Cited

U.S. PATENT DOCUMENTS 4,318,982  3/1982  Hornby et al. .
4,318,983  3/1982  Hornby et al. ................ 435/7

FOREIGN PATENT DOCUMENTS 0027631  4/1981  European Pat. Off. .
0270291  11/1987  European Pat. Off. .

OTHER PUBLICATIONS

Methods in Enzymology, vol. 122 pp. 185–192 Decker, K., "Luminometric Determination of Fad" (1986).
Daniel et al. Chem Abs. 98 158456y (1983) "Hydrolysis of FMN and FAD by alkaline phosphatase of the intestinal brush-border membrane".
Chemical Abstracts, vol. 98, No. 19, 9 May 1983 (Columbus, Ohio, US), H. Daniel et al.: "Hydrolysis of FMN and FAD by alkaline phosphatase of the intestinal brush-border membrane".

*Primary Examiner*—William H. Beisner
*Assistant Examiner*—Ralph Gitomer
*Attorney, Agent, or Firm*—Jan P. Brunelle; Walter H. Dreger

[57] ABSTRACT

Hydrolase enzymes are sensitively determined using novel substituted FAD substrates. The substituted FAD substrates are hydrolysed to FAD by the enzyme to be detected. The FAD is then combined with an apoenzyme to form a holoenzyme which is used to initiate a reaction that leads to a detectable product. When the hydrolase to be detected is phosphatase, the novel substrate is a phosphorylated derivative of FAD. A suitable apoenzyme is apo-glucose oxidase which provides exceptional sensitivity. Apo-D-amino acid oxidase, which is suitable for use in a "single pot" assay system, can also be used.

25 Claims, 2 Drawing Sheets

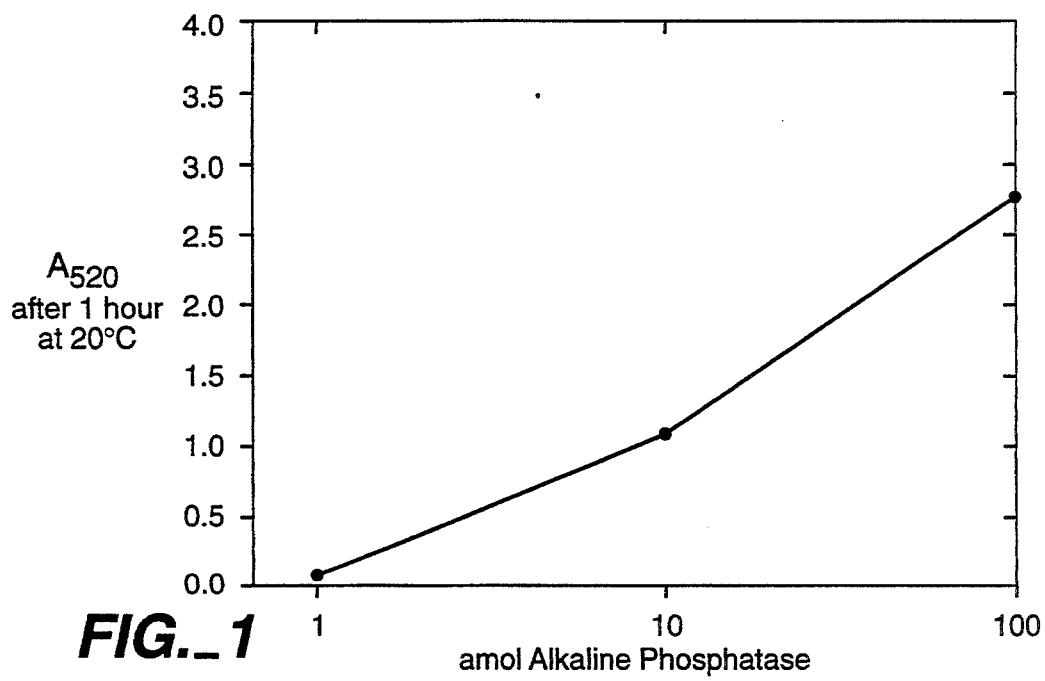
FIG._1
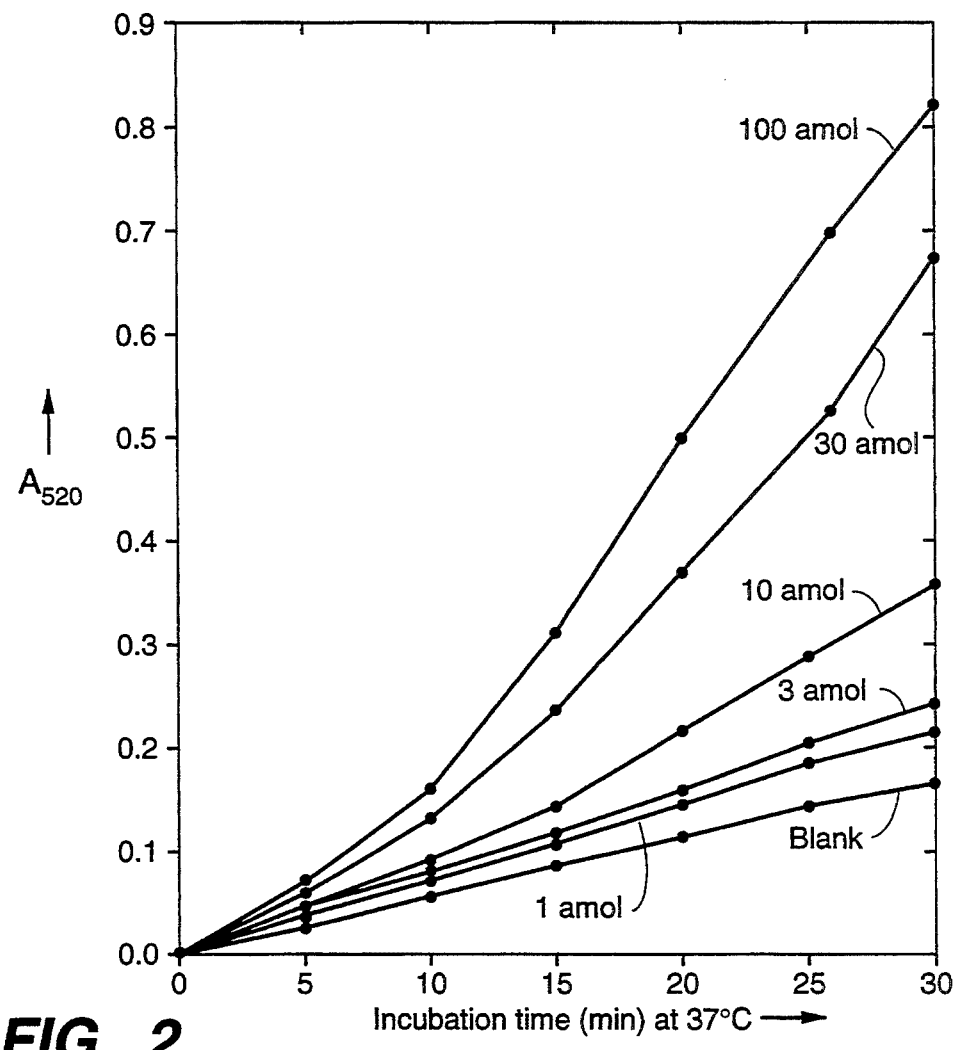
FIG._2

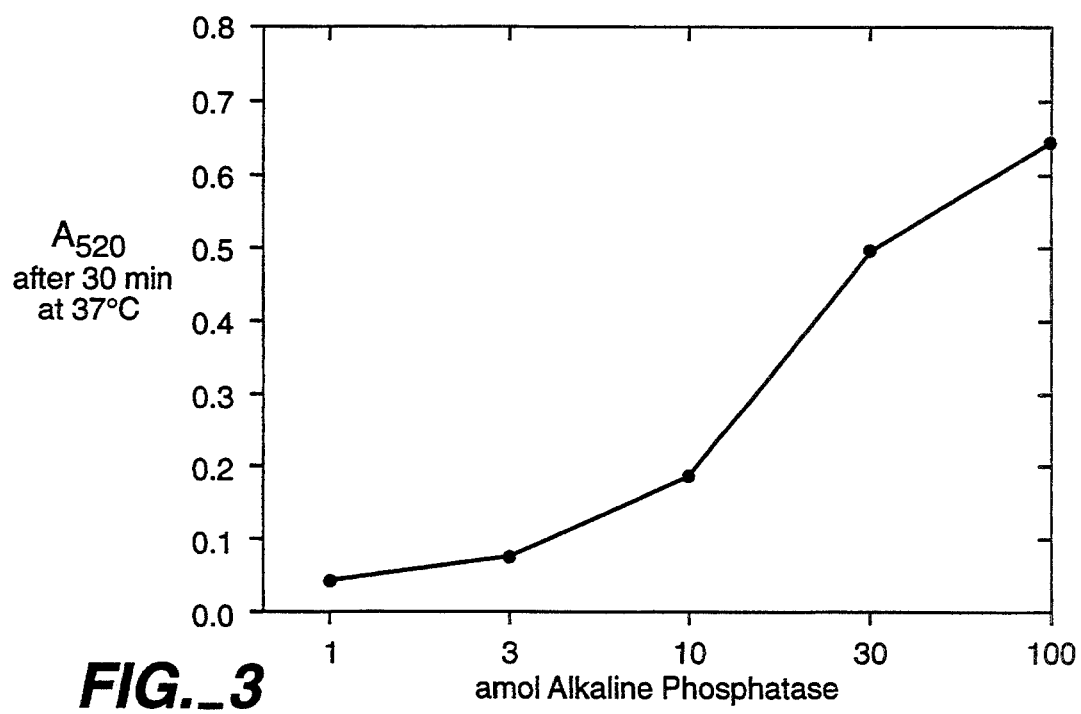
FIG._3
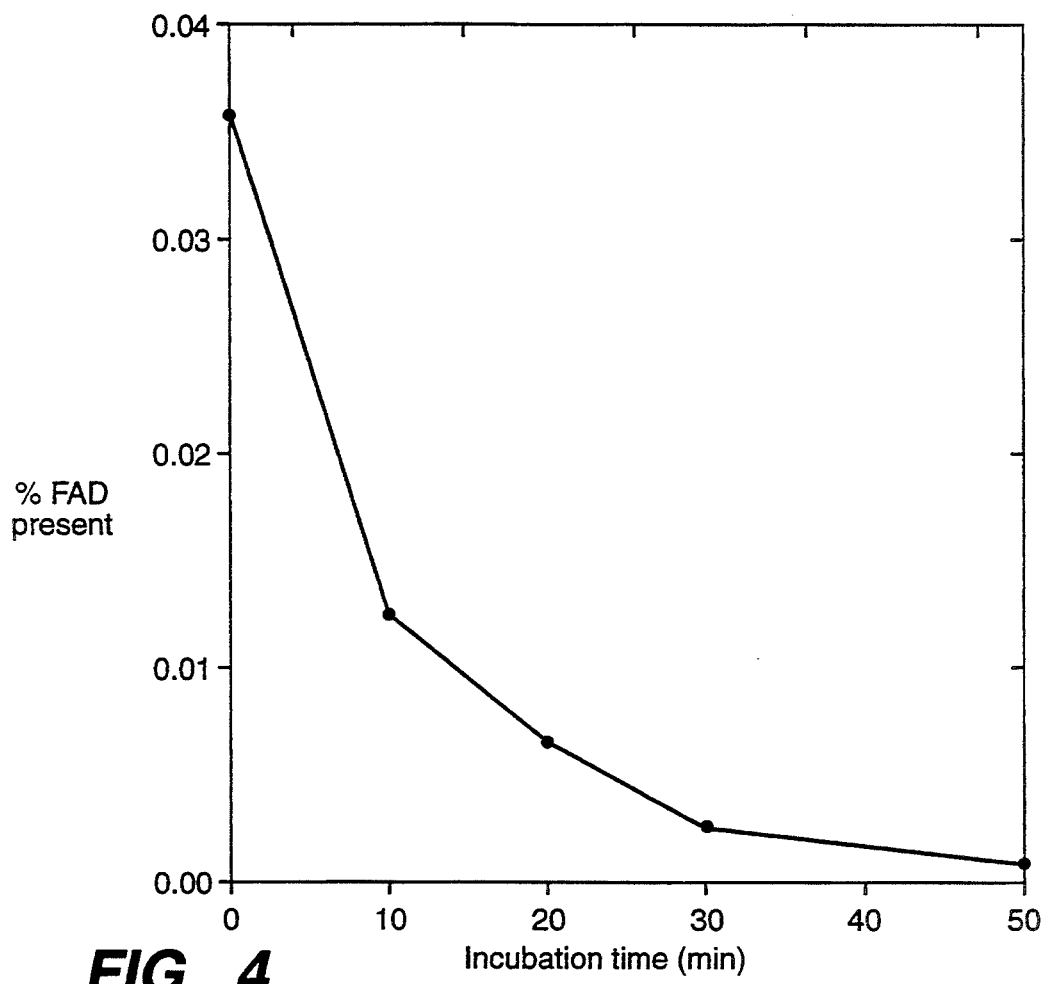
FIG._4

AMPLIFICATION ASSAY FOR HYDROLASE ENZYMES

This is a continuation of application Ser. No. 07/646,711 filed as PCT/GB89/00877, July 31, 1989, now abandoned.

BACKGROUND OF THE INVENTION

This invention relates to enzyme-linked assays.

Alkaline phosphatase (EC 3.1.3.1) is a widely used enzyme label for immunoassays and can also be employed for the determination of gene probes.

Other hydrolases have not enjoyed as wide a usage in enzyme-linked assays owing in part to the non-availability of suitable substrates for employment with them in diagnostic procedures. This invention discloses a family of novel substrates for a range of hydrolases, including alkaline phosphatase, which substrates are hydrolysed to produce a prosthetic group for a detector enzyme, thus providing a large amplification of the signal produced by the hydrolase.

A recently developed method for the assay of this enzyme relies on the hydrolysis of NADP+ in a primary stage and the subsequent cycling, in a secondary stage, of the NAD+ produced, resulting in the amplification of the signal (Johannsson et al., J. Immun. Methods, (1986), 87, 7-11, incorporated herein by reference). The technique has not as yet enjoyed widespread use on account of the relative instability of the primary substrate and enzymic cross-talk between components which can result in unacceptable background signals.

A recent technique for the sensitive detection of ribonuclease, our GB 2156518A, relies on the production of a prosthetic group or its precursor, from a prosthetogen. Typically in this methodology the primary enzyme produces riboflavin, which is subsequently converted, by use of one or more ancillary enzymes, to FMN or FAD. Either of these prosthetic groups combines with an apoenzyme to produce a catalytically active holoenzyme which in turn catalyses the signal-producing reaction. In one example the FAD converts apoglucose oxidase (EC 1.1.3.4) to the corresponding holoenzyme, which catalyses the oxidation of glucose thereby producing hydrogen peroxide which can be utilised by peroxidase (EC 1.11.1.7) to produce a coloured product (soluble or insoluble) or light (Thorpe and Kricka, Methods Enzymol. (1986), 133, 331-353, incorporated herein by reference). In another example the FAD converts apo-D-aminoacid oxidase (EC 1.4.3.3) to the corresponding holoenzyme which catalyses the oxidation of, for example, D-alanine which again results in the production of hydrogen peroxide. This can be determined colorimetrically (soluble or insoluble product), luminometrically (Decker and Hinkkanen, Methods Enzymol, (1986), 122, 185-192, incorporated herein by reference) or by using a suitable electrical or electronic biosensor.

SUMMARY OF THE INVENTION

According to the present invention there is provide a method of detecting a hydrolase enzyme (E.C. Division 3), preferably an alkaline phosphatase, which comprises using the enzyme to catalyse the formation from a prosthetogen of the prosthetic group flavin adenine dinucleotide (FAD), or an analog thereof which is capable of forming a holoenzyme, The prosthetogen being in the nature of a substituted FAD or FAD analog, the prosthetic group being produced by enzymic hydrolyric removal of The substituent; combining the FAD-type prosthetic group with an apoenzyme to form a holoenzyme, and using said holoenzyme as a catalyst in a signal-producing reaction. Depending on the exact nature of the substituent, the invention can be applied to the sensitive detection of a range of hydrolase enzymes including, but without restriction, phosphatases, phosphodiesterases, esterases, nucleases and sulfatases.

BRIEF DESCRIPTION OF THE DRAWINGS

FIG. 1. Standard curve for the estimation of alkaline phosphatase using a two-stage amplification assay with glucose oxidase as the apoenzyme detector. Both the first stage incubation with alkaline phosphatase and the second stage incubation with apoglucose were 1 hour duration. Absorbance values were plotted after subtraction of the blank reading obtained in the absence of alkaline phosphatase.

FIG. 2. Time course of color formation during the assay of alkaline phosphatase in a single-stage amplification assay using D-amino acid oxidase as the apoenzyme detector.

FIG. 3. Standard curve for the estimation of alkaline phosphatase using a one-stage amplification assay with D-amino acid oxidase as the apoenzyme detector. Absorbance values after a 30 minute incubation were plotted after subtraction of the blank reading obtained in the absence of alkaline phosphatase.

FIG. 4. Removal of FAD from FADP using apoglucose oxidase in a stirred tank ultrafiltration reactor. FAD was estimated from the activity of reconstituted hologlucose oxidase in samples withdrawn periodically from the reactor.

DETAILED DESCRIPTION OF THE INVENTION

In a preferred embodiment, the prosthetogen is an FAD-phosphate (FADP) and the hydrolase is a phosphatase. This procedure has the great advantage that the prosthetic group, FAD, is formed directly by action of a phosphatase enzyme on the prosthetogen, FADP, without the necessity to add any ancillary converting enzymes. The effectiveness and practical utility of the invention in relation to phosphatase enzymes are greatly enhanced by the additional discovery and identification of shelf-stable apoenzymes, two of which are given by example, for which the prosthetogen, FADP, despite its prosthetic group-like structure, has two important properties: it possesses no significant activity per se as a prosthetic group (which would cause high background signals), and it does not significantly interfere with the formation of the holoenzyme from apoenzyme and FAD (which would reduce the sensitivity of the system).

Suitable apoenzymes include apo-D-aminoacid oxidase and apoglucose oxidase as mentioned above, as well as apo-L-aminoacid oxidase, apoxanthine oxidase and other apoenzymes which will be apparent to those skilled in the art. Apo-D-aminoacid oxidase is a preferred apoenzyme for many applications since it is very shelf-stable, and has kinetic characteristics that permits the technology to be used in a 'single pot' format, with all components added as a single promix to analyte-linked alkaline phosphatase. Suitable substrates for it are D-alanine, D-methionine and D-proline. For maximising the sensitivity of the invention without incorporating tail-end cycling components (see below), the use of apoglucose oxidase is advantageous, although its use requires a two stage format in which the first stage, involving hydrolysis of FADP, is operated at pH 8.0 and the second detection stage at a lower pH.

If desired the sensitivity of the signal-producing detection system based on apo-D-aminoacid oxidase may be greatly enhanced, but at the expense of increased complexity, by using "tail end cycling". In this procedure the holoenzyme may be used to catalyse a reaction which leads to the production of a cyclable substrate which generates a detectable product. For most applications, involving determination of greater than 0.01 attomoles of alkaline phosphatase in about one hour, The additional cycling procedure is not required. It would, however, be advantageous in diagnostic procedures that require detection of a very small number of virus particles or genes (as, for example, in direct procedures for HIV).

The reaction leading to the production of the cyclable substrate may itself give rise to a detectable side product. For example, hydrogen peroxide may be generated which may be detected using horseradish peroxidase to produce a signal. Examples of holoenzyme-catalysed reactions resulting in the generation of hydrogen peroxide were also given above.

The side product generated may be the same as that generated in the reaction leading to the production of the cyclable substrate and may therefore be detected in the same way, an additive effect being produced by the two processes.

Prosthetogen Substrates for Phosphatases

FAD may suitably carry a phosphate group at any one or more of the positions labelled A—E in formula I below.

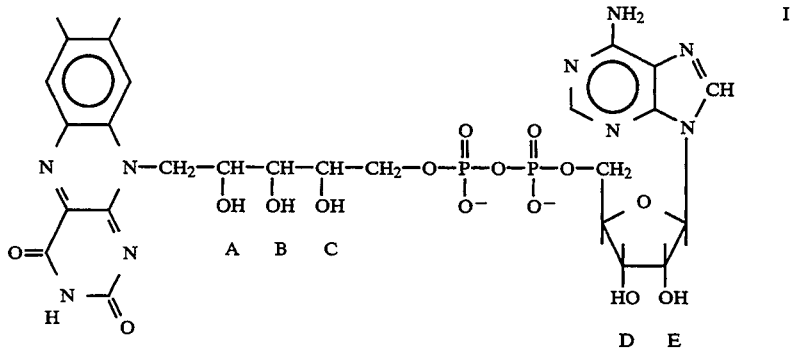

However, any phosphorylated FAD analog which, after hydrolysis by phosphatase, yields an FAD analog which acts as a prosthetic group for an apoenzyme may be employed. Possibilities for FAD analogs include those in which a hydroxy group for carrying phosphate is provided on the aromatic nucleus of either or both of flavine or adenine or on a substituent of these nuclei. For example hydroxYalkyl substituents might be provided on the unsubstituted positions of the flavine benzene ring. Alternatively the flavine and/or adenine rings in FADP could be altered structurally in other ways that could be advantageous. Preferably, however, an FAD analog in which a hydroxymethyl group is provided in place either or both of the flavine methyl groups is used. For each analog, phosphate groups may then be provided on one or more of the hydroxy groups present. Thus, where two hydroxymethyl groups are present in the flavine of FAD either, both or neither of these may carry a phosphate group in the phosphorylated analog.

These compounds are novel and provide a further aspect of the present invention. The invention also provides a method for the synthesis of these compounds. A suitable method includes conversion of an FADP precursor having a protected phosphate group into FADP. The phosphate group may be protected as a diphenyl phosphate group, for example as shown in the Reaction Scheme below.

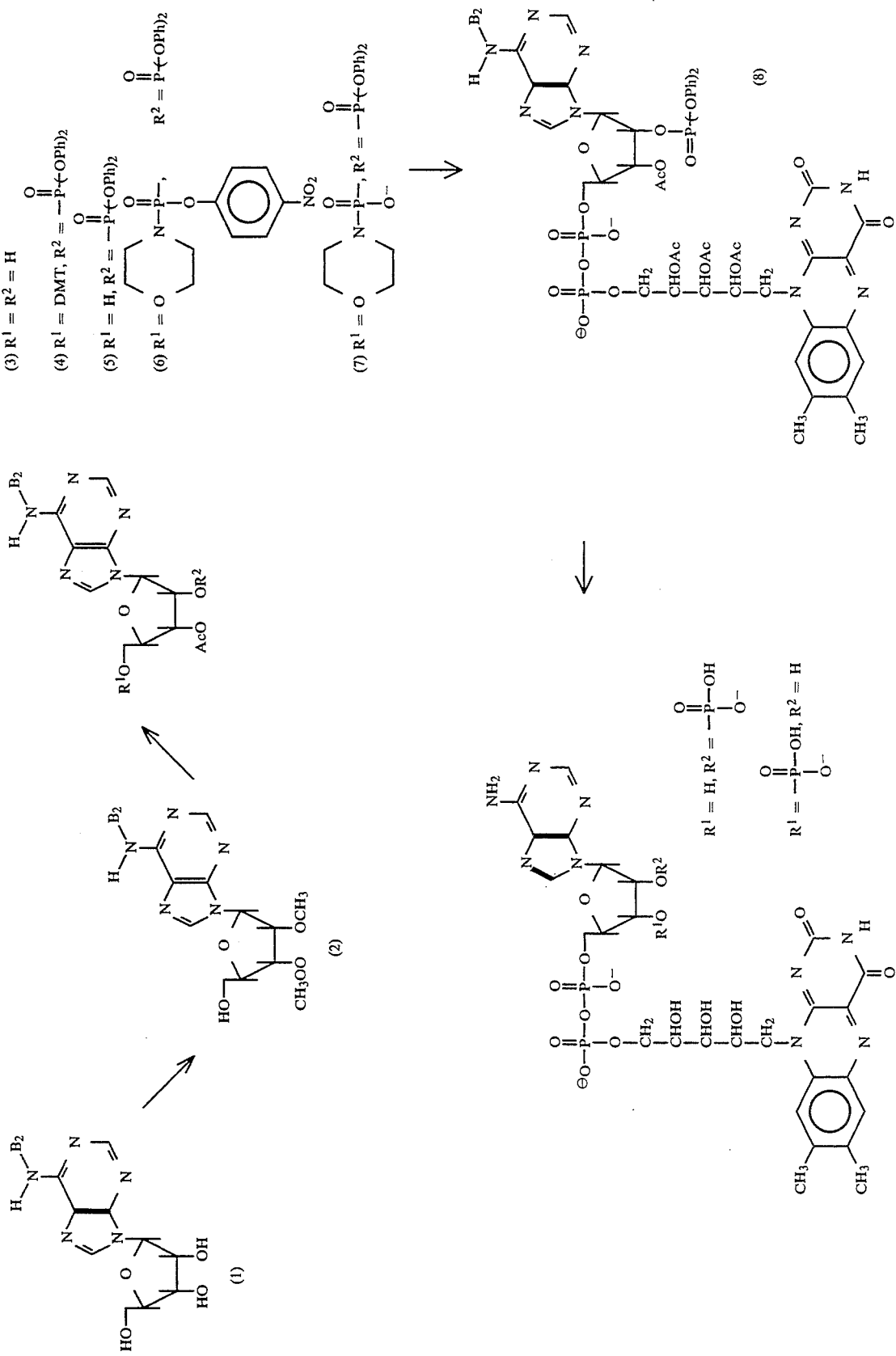

Compounds having a phosphate geoup at the 2' and-/or 3' position of the sugar molecule are preferred for use in assay methods of the present invention.

The phosphatase can itself be the primary analyte, or it can be part of an assay procedure for detecting another analyte.

Other Hydrolase Enzymes and Substrates for Use in the Invention

Some appropriate enzyme/substrate pairs are listed by example only in the following Table.

FADX is the substrate with —OX replacing an —OH in one or more of positions A, B, C, D or E of formula I or the hydroxyl group of a suitable hydroxyl-containing analog of FAD (see above).

| Enzyme (EC number) | X—OH | Preferred position in formula I |
|---|---|---|
| phosphatase (3.1.3.1 and 3.1.3.2) | Phosphate $\begin{array}{c}O\quad OH\\ \diagdown\diagup\\ P\\ \diagup\diagdown\\ -O\quad OH\end{array}$ | D or E |
| Sulfatase (3.1.6.1) | Sulfate $^-O-SO_2-O-H$ | None |
| Carboxylesterase (3.1.1.1) | Carboxylic acid $R-C\begin{array}{c}OH\\ \diagup\\ \diagdown\\ O\end{array}$ | None |
| Acetyl-esterase (3.1.1.6) | Acetic Acid $CH_3-C\begin{array}{c}OH\\ \diagup\\ \diagdown\\ O\end{array}$ | None |
| Venom phosphodiesterase (3.1.15.1) | Nucleoside or deoxnucleoside 5'-phosphate $R-O-P\begin{array}{c}O\\ \diagup\\ -OH\\ \diagdown\\ O^-\end{array}$ | D |

The invention also includes kits for carrying out the method hereof. A suitable kit may comprise an FAD substrate for the enzyme being detected, and a signal producing system for detecting the presence of FAD, Examples of suitable signal producing systems include those referred to above.

The invention will be more particularly illustrated, by way of example only, with reference to the following Examples.

EXAMPLE 1

Preparation of FAD-2' (3')-Phosphate

Preparation A

N-benzoyladenosine (1) was transformed into the 3'-acetate (3) by reaction with excess trimethylorthoacetate and p-toluenesulphonic acid, followed by rearrangement of the intermediate orthoester with 50% acetic acid. The crude 3'-acetate was purified by flash chromatography over $SiO_2$ (230–400 mesh) with $CHCl_3$—MeOH 93:7 and treated successively with 4,4'-dimethoxytritylchloride and diphenylphosphochloridate in pyridine. After concentration the residue was dissolved in dichloromethane and reacted with excess dichloroacetic acid. The crude product was purified as before [$SiO_2$(230–400 mesh) with $CHCl_3$—MeOH 96:4] to give N-benzoyl-3'-acetyladenosine-2'-diphenylphosphate (5). On reaction of (5) with 4-nitrophenyl-4-morpholinophosphochloridate and 1-methylimidazole in $CH_3CN$ the protected morpholinophosphate (6) was obtained, which was purified as before [$SiO_2$ (230–400 mesh) with $CHCl_3$—MeOH 97:3]. Deprotection was achieved by reaction with tetra-n-butylammonium acetate and the morpholinophosphate (7) formed was coupled with excess triacetyl-FMN in DMF at 50° C. for 18 h.

Deprotection of the crude product was accomplished by reaction with conc $NH_3$-ethanol 4:1 for 36 h at room temperature. The reaction mixture was concentrated until neutral, dissolved in 0.01 N HCl and extracted with $CHCl_3$ (3x). The pH of the solution was adjusted to 2 with 1N HCl and the solution stirred for 2 h in order to hydrolyse any 2',3'-cyclic phosphate that may have formed.

After addition of excess $NH_3$ the solution was concentrated till neutral and then lyophilised.

Crude 2'(3')-FADP was isolated by FPLC on a Mono Q HR 10/10 anion exchange column (Pharmacia) with a $H_2O$/1M ammonium formate (pH 6.5) gradient. The fractions eluting with 0.65–0.8M ammonium formate were pooled and freeze-dried. This material was further purified by anion exchange chromatography which under the same conditions as above gave a fraction eluting at: 0.65–0.8M ammonium formate, which after freeze-drying and redissolving in 10 mM Tris buffer (pH 8.0, 1 mM Mg $Cl_2$, 0.1 mM $ZnCl_2$) was acted upon by alkaline phosphatase to give a product that eluted in the same place as FAD and was able to reconstitute apoglucose oxidase. Traces of FAD could be removed by treatment with a suitable apoenzyme followed by ultrafiltration to remove the macromolecules.

Preparation B

Crude 2'(3')-FADP can also be prepared by coupling of adenosine 2',3'-cyclic phosphate 5'-phosphoromorpholidate (9) (J. G. Moffatt and H. G. Khorana, J. Amer. Chem. Soc., 83 (1961) 663, incorporated herein by reference) with triacetyl FMN, followed by $NH_3$deprotection, HCl treatment and purification as described above.

Alternatively, adenosine 2'3'-cyclic phosphate 5'-phosphate (10) (A. Simoncsits and J. Tomasz, Biochem. Biophys. Acta. 395 (1975) 74, incorporated herein by reference) was converted to (9) by reaction with dicyclohexylcarbodiimide and morpholine and then coupled, deprotected and purified as above.

These procedures are shown by the following reaction scheme.

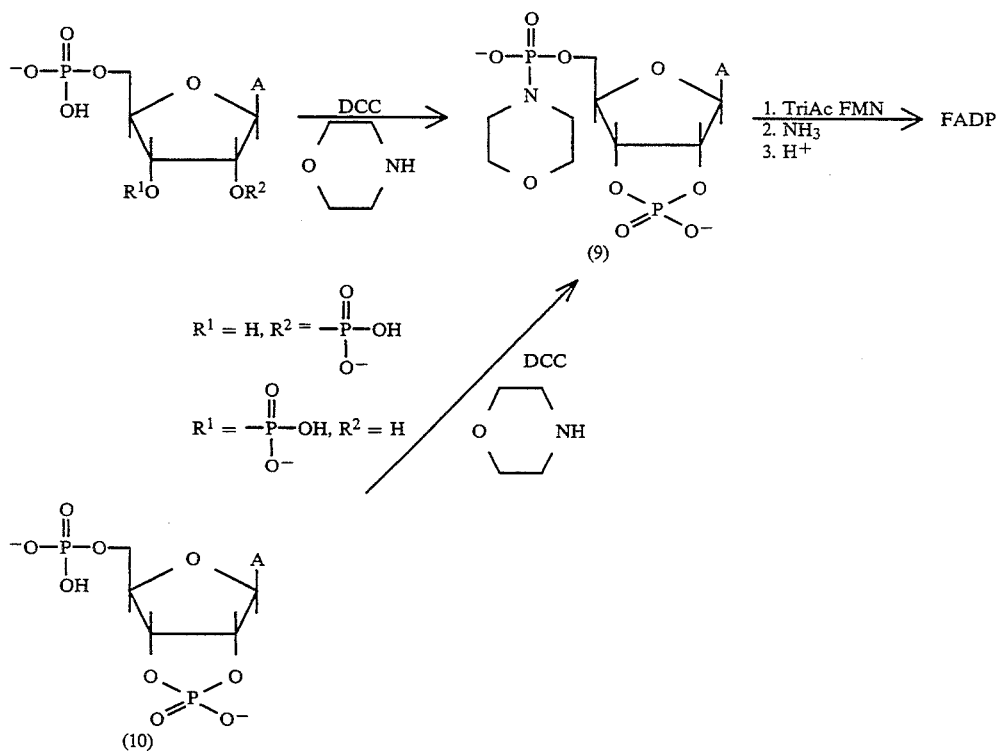

EXAMPLE 2

(Alkaline) Phosphatase Assay

A. Colorimetric Assay Using Apoglucose Oxidase Detector

In these experiments, the FADP used contained 0.036% FAD. In order to reduce the background signal to an acceptable level, the glucose concentration in the second incubation mixture was reduced to 10% of its optimal value.

A typical mixture for the assay of alkaline phosphatase is as follows:

0.2 M Tris-HCl buffer pH 8.0 containing 1 mM $MgCl_2$ and 0.1 mM $ZnCl_2$
0.2 mM FAD-phosphate Alkaline phosphatase
Total Volume 0.05 mL The mixture is incubated at room temperature for 1 hour, and then a further 0.05 mL of the following mixture added:

| | |
|---|---|
| 0.2 µM | apoglucose oxidase |
| 0.01 M | glucose |
| 6 µg | peroxidase |
| 16 mM | 3,5-dichloro-2-hydroxybenzene-sulphonic acid |
| 1.6 mM | 4-aminoantipyrine |
| 0.3 M | Bis-Tris pH 6.1 |

Total volume 0.1 mL, pH 7.0. The development of colour was followed at 520 nm. After an initial lag due to the reconstitution of the apoglucose oxidase, colour production is linear with time. FIG. 1 shows the absorbance obtained after subtraction of a control sample containing no alkaline phosphatase for an incubation time of 1 hour at room temperature with different amounts of alkaline phosphatase. Under these conditions, 1 amol of alkaline phosphatase could be detected.

B. Colorimetric Assay Phosphatase Using apo-D-amino Acid Oxidase Detector

Use of apo-D-amino acid oxidase, whose holoenzyme has a pH optimum of 8.0–9.0, allows the above assay to be conducted in a single pot:

| | |
|---|---|
| 0.1 M | Tris-HCl buffer pH 8.0 containing 1 mM $MgCl_2$ and 0.1 mM $ZnCl_2$ |
| 0.1 mM | FADP |
| 0.1 µM | apo-D-amino acid oxidase |
| 35 mM | D-alanine |
| 8 mM | 3,5-dichloro-2-hydroxybenzene sulphonic acid |
| 0.8 mM | 4-aminoantipyrine |
| 6 µg | peroxidase alkaline phosphatase Total volume 0.1 mL |

The above ingredients may be mixed beforehand and added directly too the alkaline phosphatase. FIG. 2 shows how the absorbance increases with time at 37° C. in the presence of different amounts of alkaline phosphatase. The final absorbance after subtraction of the blank for an incubation time of 30 min is shown in FIG. 3. Again 1 amol of alkaline phosphatase could easily be detected.

D-amino acid oxidase shows activity with a range of amino acids, and a higher rate of oxidation was achieved using D-methionine or D-proline at the same concentration. The rates relative to D-alanine were 2.5 and 3.0 respectively.

EXAMPLE 3

Preparation of Enzymes

A. Preparation of Apoglucose Oxidase

Apoglucose oxidase was prepared according to the method of Morris and Buckler (Methods Enzymol.

(1983) 92, 413–425, incorporated herein by reference) and final traces of holoenzyme removed by a treatment with phenylacetic acid; a procedure based on the information presented by Hemmerich et al (Nature (1967), 213, 728–730), incorporated herein by reference). The apoenzyme may be stabilised with a suitable antibody to the holoenzyme (Morris, Anal. Biochem. (1985), 151, 235–241, incorporated herein by reference).

B. Preparation of apo-D-amino Acid Oxidase

Apo-D-amino acid oxidase was prepared according to the procedure described by Brumby and Massey (Biochem. Prep. (1968), 12, 29–41, incorporated herein by reference). Residual holoenzyme was removed by absorbing the apoenzyme onto Blue Sepharose, washing away unbound holoenzyme, and subequently eluting the apoenzyme (Leonil et al J. Chromatography (1985), 347, 316–319, incorporated herein by reference). The enzyme was desalted against 20 mM Bis Tris propane buffer pH 7.0 containing 5 g/L mannitol, aliquoted, and freeze-dried.

C. Preparation of Phosphatase-Free Peroxidase

Commercially obtained peroxidase was found to contain varying levels of phosphatase. This was removed by dissolving the peroxidase in 20 mM Bis Tris propane at pH 7.0 containing 5 g/L mannitol and passing the mixture through a calcium phosphate/cellulose gel equilibrated with the same buffer, whereupon the phosphatase contaminants were removed. The eluate was aliquoted and freeze-dried.

EXAMPLE 4
Removal of Traces of FAD from FADP

Remaining traces of FAD were removed using apoglucose oxidase, which binds FAD tightly, but does not bind FADP.

A. Stirred-Tank Ultrafiltration Reactor Using Soluble Apoglucose Oxidase

Apoglucose oxidase (2.5 μM) was mixed with FADP (200 μM) at room temperature. The decline in the amount of residual FAD as a proportion of the amount of FADP present with time is shown in FIG. 4. After 30 min the mixture was ultrafiltered to yield a sample of FADP containing less than 0.002% FAD.

B. Packed-Bed Plug-Flow Reactor Using Immobilised apo-glucose Oxidase

Free amino groups were introduced into glucose oxidase as described by Royer ( Methods Enzymol., (1987), 135, 141–146, incorporated herein by reference). This derivatised enzyme (25 mg) was mixed with TresylSepharose 4B (5 mL) in 0.1 M sodium bicarbonate, containing 0.5M NaCl, and gently agit. ated for 16 h at 4° C. After blocking unreacted tresyl groups, the gel was packed into a column (6 mm×10 mm dia) and treated with 1 mL 25 mM phosphate, pH 1.1, containing 20% glycerol to remove the prosthetic group. This was immediately followed by 20 mL 1M phosphate buffer, pH 7.0. The column was equilibrated with 20 mM Bis Tris propane, pH 7.0, and 10 mL 5 mM FADP in the same buffer was percolated through the column at 0.61 mL/min in a closed loop configuration. The proportion of FAD was reduced from 0.034% to 0.0034% of FADP after 18 minutes at 4° C.

In the next four Examples alkaline phosphatase is used to catalyse the hydrolysis of FADP to yield FAD. The FAD produced subsequently combines with apo-D-aminoacid oxidase (apo DAO) to yield holo-D-aminoacid oxidase (holo DAO). In the absence of any cycling the signal producing system relies on the use of holo-DAO to catalyse the conversion of D-alanine to pyruvate with the generation of hydrogen peroxide. With cycling (shown in the diagrams below the broken line), pyruvate or a product generated from pyruvate is interconverted with another compound, the interconversion reactions generating detectable hydrogen peroxide.

Example 5

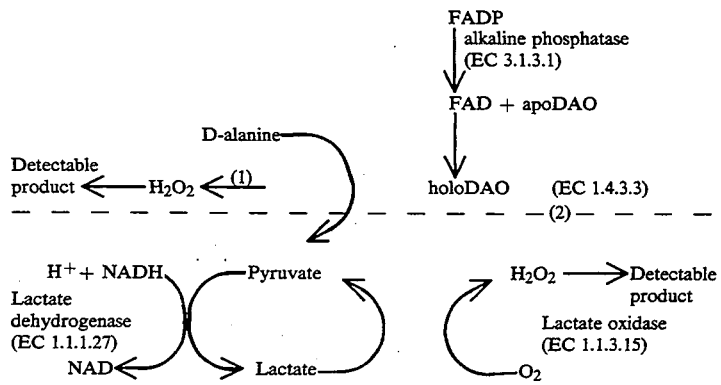

The following pyruvate-L-lactate cycling system was set up in a total volume of 1 ml.
  0.2M Tris HCl, pH 8.0
  1 mM $Mg^{2+}$
  0.1 mM $Zn^{2+}$
  1 mM NADH
  2 mM 3,5-dichloro-2-hydroxybenzenesulphonic acid
  0.2 mM 4-aminoantipyrine
  60 μg/ml horse radish peroxidase
  10 units Lactate dehydrogenase
  1.3 units (0.1 mg) Lactate oxidase from *Pediococcus sp.*

The absorbance of the solution at 520 nm was monitored. Then pyruvate was added to the reaction mixture and the rate of change of absorbance monitored. The results are indicated in the table below.

| Concentration of Pyruvate | Rate: change in absorbance/min | | |
|---|---|---|---|
| | Background | After pyruvate addition | Net Rate |
| 100 μm | 0.0124 | 0.564 | 0.552 |

-continued

| | Rate: change in absorbance/min | | |
|---|---|---|---|
| Concentration of Pyruvate | Background | After pyruvate addition | Net Rate |
| 10 μm | 0.0118 | 0.0822 | 0.0704 |

The results indicate that pyruvate-lactate cycling is possible in the presence of lactate dehydrogenase and lactate oxidase and results in the generation of detectable hydrogen peroxide.

Other cycling systems that could be used include those illustrated by the following reaction schemes. In each case the eventual colour-forming process involves the $H_2O_2$ produced participating in a peroxidase-catalysed reaction.

Example 6

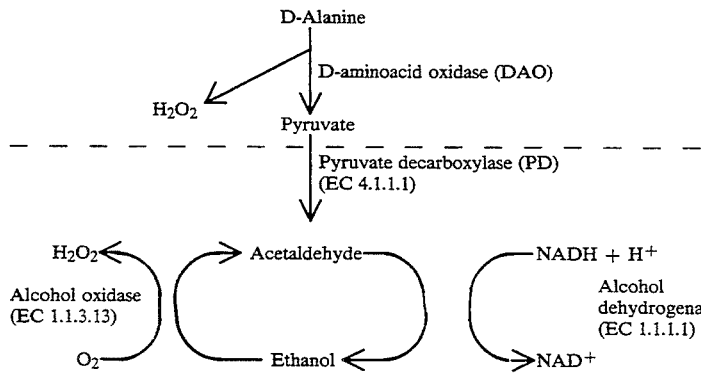

Example 7

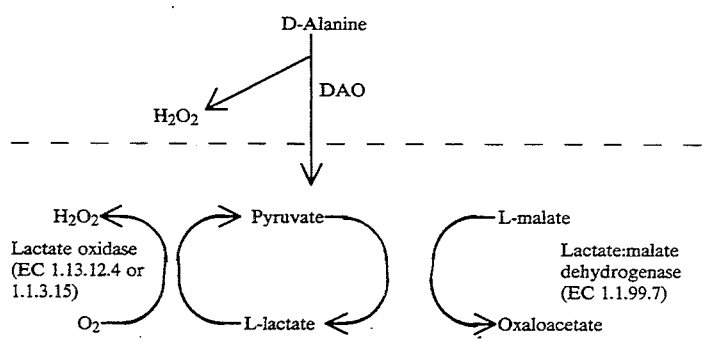

Example 8

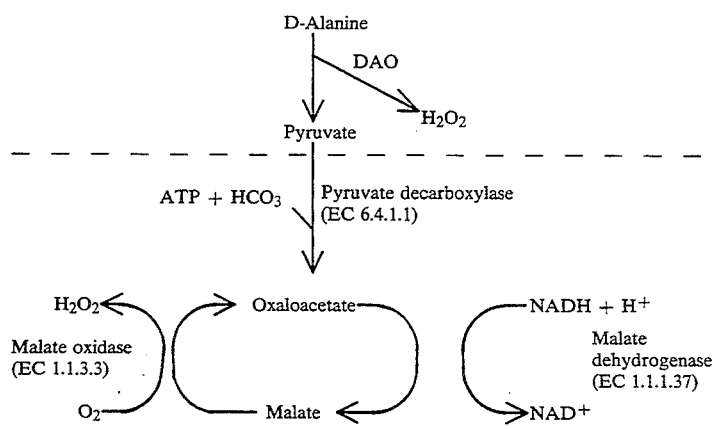

Of the systems so far described, those based on the enzymes DAO and GOD are preferred for use without tail-end cycling.

DAO has the advantage that it can function effectively at pH 8, which is also suitable for alkaline phosphatase. Thus, the components of the assay can all be premixed, forming a "one-pot" assay system which is very convenient.

GOD has the advantage of forming a very stable holoenzyme with a high turnover number. Its use produces an assay of very high sensitivity, but is best operated as a two-pot system since GOD works best below the pH 8.0 which is best suited for the phosphatase being detected.

We claim:

1. A method of detecting a hydrolase enzyme which comprises combining a sample suspected of containing said hydrolase enzyme with a flavin adenine dinucleotide (FAD) substituted with a substituent or an analog of an FAD substituted with a substituent to hydrolytically remove said substituent to form an FAD or FAD analog when said hydrolase enzyme is present in said sample, combining said FAD or FAD analog with an apoenzyme to form a holoenzyme, and combining said holoenzyme with a substrate for said holoenzyme to produce a detectable product.

2. A method according to claim 1 wherein the hydrolase enzyme is a phosphatase enzyme and said substituent is phosphate.

3. A method according to claim 1 wherein the apoenzyme is apo-D-aminoacid oxidase (apo-DAO), and said holoenzyme is holo-DAO.

4. A method according to claim 3 wherein said substrate is an amino acid and said detectable product is $H_2O_2$.

5. A method according to claim 4 wherein said amino acid is selected from the group consisting of D-alanine, D-methionine and D-proline.

6. A method according to claim 3 wherein said FAD substituted with a substituted with a substituent or a analog of FAD substituted with a substituent and said apo-DAO are premixed and added to said sample.

7. A method according to claim 1 wherein the apoenzyme is apo-glucose oxidase (apo-GOD).

8. A method according to claim 7 wherein said substrate is glucose and said detectable product is $H_2O_2$.

9. An assay kit for detecting a hydrolase enzyme comprising an FAD Substituted with a substituent or an analog of an FAD substituted with a substituent said substituent capable of being hydrolyzed by said hydrolase enzyme to produce an FAD or an analog of FAD, an apoenzyme capable of forming a holoenzyme with said FAD or said analog of FAD, and a substrate capable of reacting with said holoenzyme to generate a detectable product.

10. An assay kit according to claim 9 wherein said substituent is phosphate.

11. An assay kit according to claim 9 wherein the apoenzyme is apo-DAO, and said holoenzyme is holo-DAO.

12. An assay kit according to claim 11 wherein said substrate is an amino acid and said detectable product is $H_2O_2$, said assay kit further comprising a means for detecting $H_2O_2$.

13. An assay kit according to claim 12 wherein said amino acid is selected from the group consisting of D-alanine, D-methionine and D-proline.

14. An assay kit according to claim 11 wherein said FAD substituted with a substituent or an analog of FAD substituted with a substituent, said apoenzyme and said substrate capable of reacting with said holoenzyme, are in a premixed form.

15. An assay kit according to claim 9 wherein said apoenzyme is apo-GOD, and said holoenzyme is holo-GOD.

16. An assay kit according to claim 15 wherein said FAD substituted with a substituent or an analog of FAD substituted with a substituent end said ape-GOD are separate from said aubstrate capable of reacting with said hole-GOD, so that said FAD or said analog of FAD is formed in a reaction that can be carried out separately from a reaction between said hole-GOD and said substrate capable of reacting with said hole-GOD.

17. An FAD substituted with a substituent or analog of an FAD substituted with a substituent, said substituent being capable of hydrolytic removal by an E.C. Division 3 hydrolase enzyme to give an FAD or an FAD analog capable of forming a holoenzyme from an apoenzyme.

18. An FAD substituted with a substituent or an analog of FAD substituted with a substituent according to claim 17 wherein said substituent is located at at least one of the 2' and 3' positions of the ribose moiety of said FAD substituted with a substituent or said analog of FAD substituted with a substituent.

19. An FAD derivative substrate for a hydrolase enzyme, said derivative having the formula:

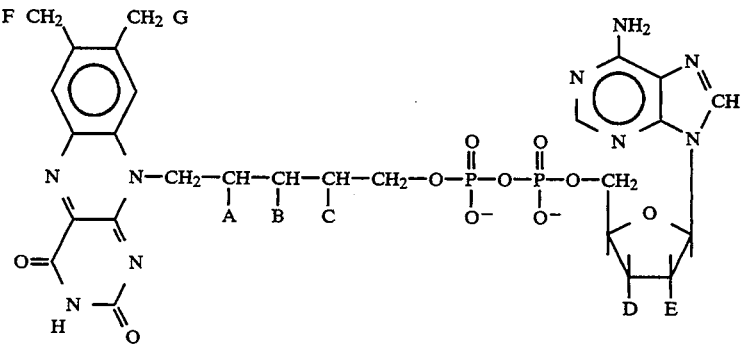

wherein each A, B, C, D and E is independently selected from hydroxy and substituent X, each F and G is independently selected from hydrogen, hydroxy and substituent X, with the proviso that at least one of A, B, C, D, E, F and G is substituent X, and where X is a substituent capable of removal by an E.C. Division 3 hydrolase to form a hydroxy group.

20. An FAD derivative substrate of claim 19 wherein said substituent X is a phosphate substituent and said E.C. Division 3 hydrolase enzyme is a phosphatase enzyme.

21. A method of producing an FAD derivative substrate of claim 19 which comprises:
hydrolyzing a precursor of solid FAD derivative substrate in which at least one of A—G is a said substituent X protected against hydrolysis, and any of A—G which is not a protected substituent X is a group hydrolyzable to a hydroxy group; and removing the substituent X protection.

22. An FAD derivative substrate of claim 19 wherein said substituent X is a sulfate substituent and said E.C. Division 3 hydrolase enzyme is a sulfatase enzyme.

23. An FAD derivative substrate of claim 19 wherein said substituent X is a carboxylic acid and said E.C. Division 3 hydrolase enzyme is a carboxylesterase enzyme.

24. An FAD derivative substrate of claim 19 wherein said substituent X is an acetic acid substituent and said E.C. Division 3 hydrolase enzyme is an acetyl esterase enzyme.

25. An FAD derivative substrate of claim 19 wherein said substituent X is a nucleoside or deoxynucleoside 5'-phosphate substituent and said E.C. Division 3 hydrdlase enzyme is a phosphodiesterase esterase enzyme.

* * * * *